United States Patent [19]

Lyman et al.

[11] Patent Number: 5,084,246
[45] Date of Patent: Jan. 28, 1992

[54] MULTI-WELL TEST PLATE

[75] Inventors: George Lyman, Cape Porpoise, Me.; Anthony Labriola, Woburn, Mass.

[73] Assignee: Costar Corporation, Cambridge, Mass.

[21] Appl. No.: 923,906

[22] Filed: Oct. 28, 1986

[51] Int. Cl.$^5$ .............................................. G01N 21/03
[52] U.S. Cl. ................................... 422/101; 422/102; 436/165; 436/177; 436/809; 356/246; 435/301; 435/809
[58] Field of Search ............... 422/102, 99, 58, 101, 422/104; 436/809, 810, 165, 177, 180; 356/244; 435/300, 301, 311, 809

[56] References Cited

U.S. PATENT DOCUMENTS

| | | | |
|---|---|---|---|
| 3,378,347 | 4/1968 | Saravis | 422/58 |
| 3,378,481 | 4/1968 | Saravis et al. | 422/58 X |
| 3,389,966 | 6/1968 | Saravis | 422/58 X |
| 3,390,962 | 7/1968 | Goldsmith | 422/58 |
| 3,649,464 | 3/1972 | Freeman | 422/99 X |
| 3,806,422 | 4/1974 | Moyer et al. | 435/26 X |
| 4,154,795 | 5/1979 | Thorne | 422/102 X |
| 4,319,841 | 3/1982 | Suovaniemi et al. | 422/102 X |
| 4,545,958 | 10/1985 | Dopatka | 422/102 |

FOREIGN PATENT DOCUMENTS

| | | | |
|---|---|---|---|
| 2435317 | 2/1976 | Fed. Rep. of Germany | 356/246 |
| 02775 | 7/1984 | Finland | 356/246 |

OTHER PUBLICATIONS

Fisher Scientific 1983, Fakon 96-Well Flexible Microplates, pp. 699 & 1185.

Primary Examiner—Lynn Kummert
Attorney, Agent, or Firm—Wolf, Greenfield & Sacks

[57] ABSTRACT

A multi-well test plate which includes a base and a plurality of well strips. The well strips are removable from the base and the individual wells of each strip are separable. The wells in each strip are joined by T-shaped connecting members which hold the wells in a flat linear array when the well strips are either held in or removed from the base and the T-shaped members are readily severable to permit easy separation of individual wells.

4 Claims, 3 Drawing Sheets

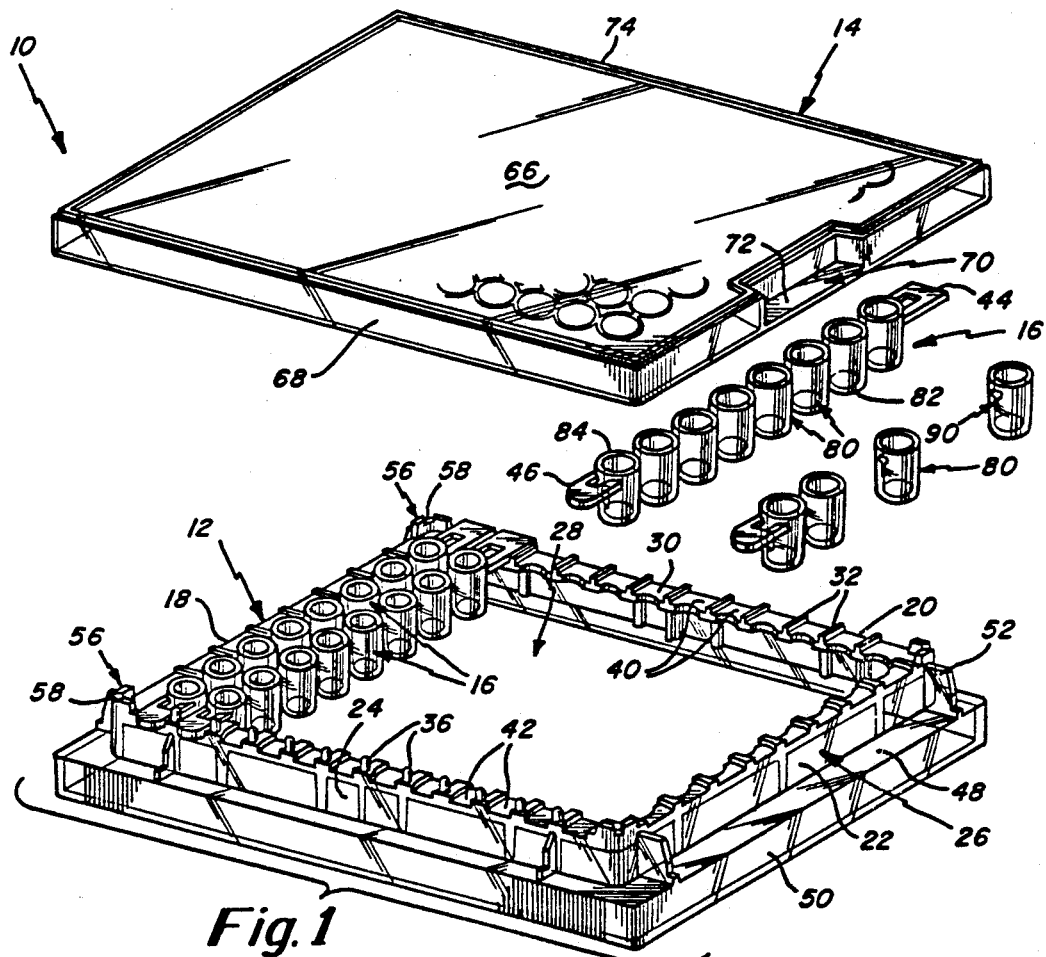
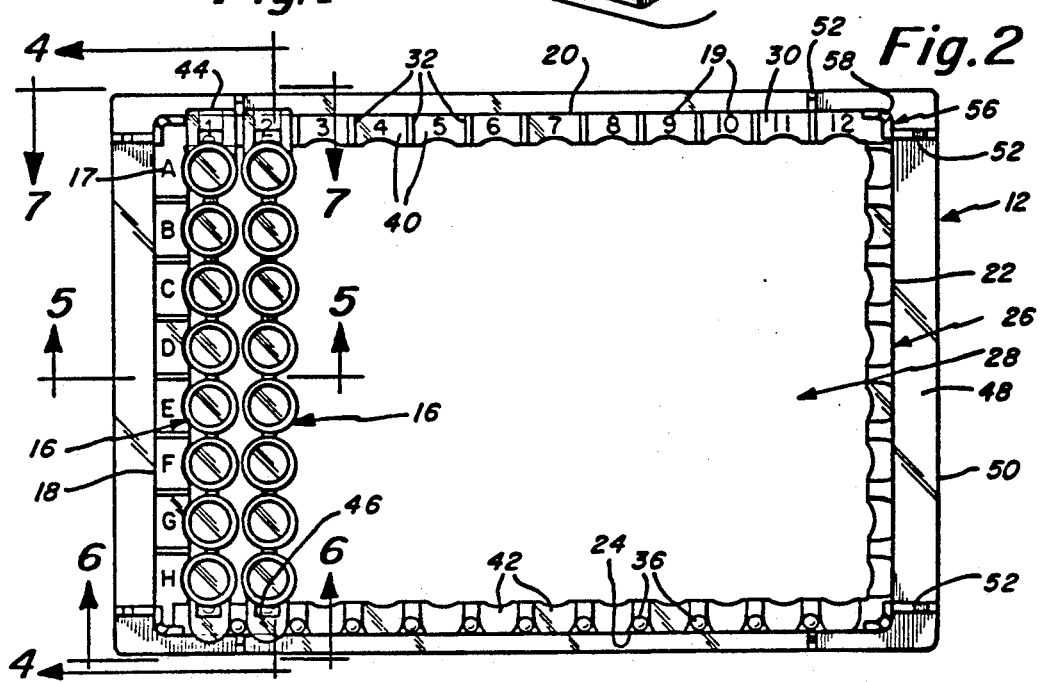

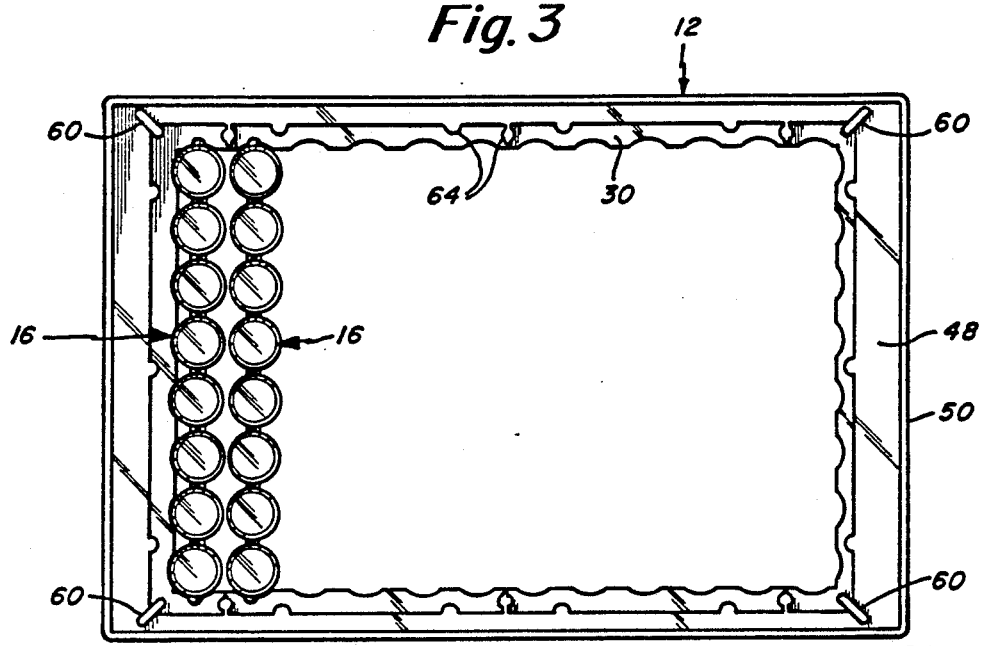
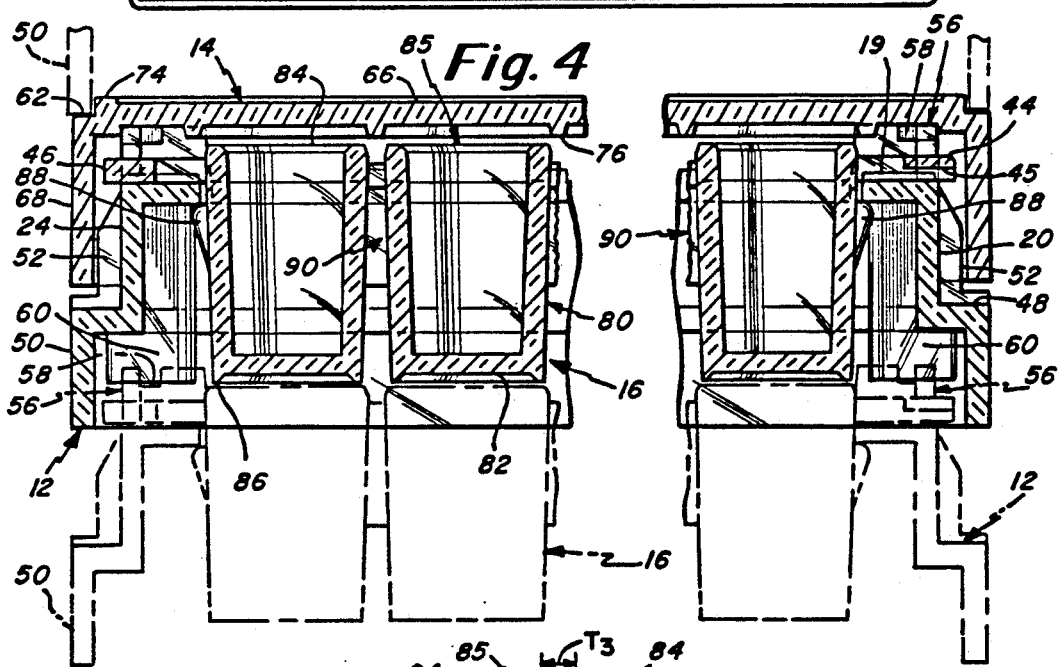
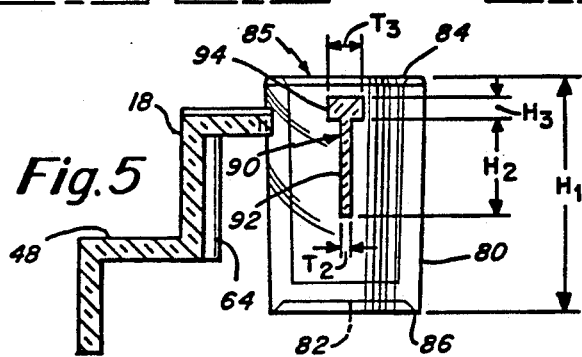

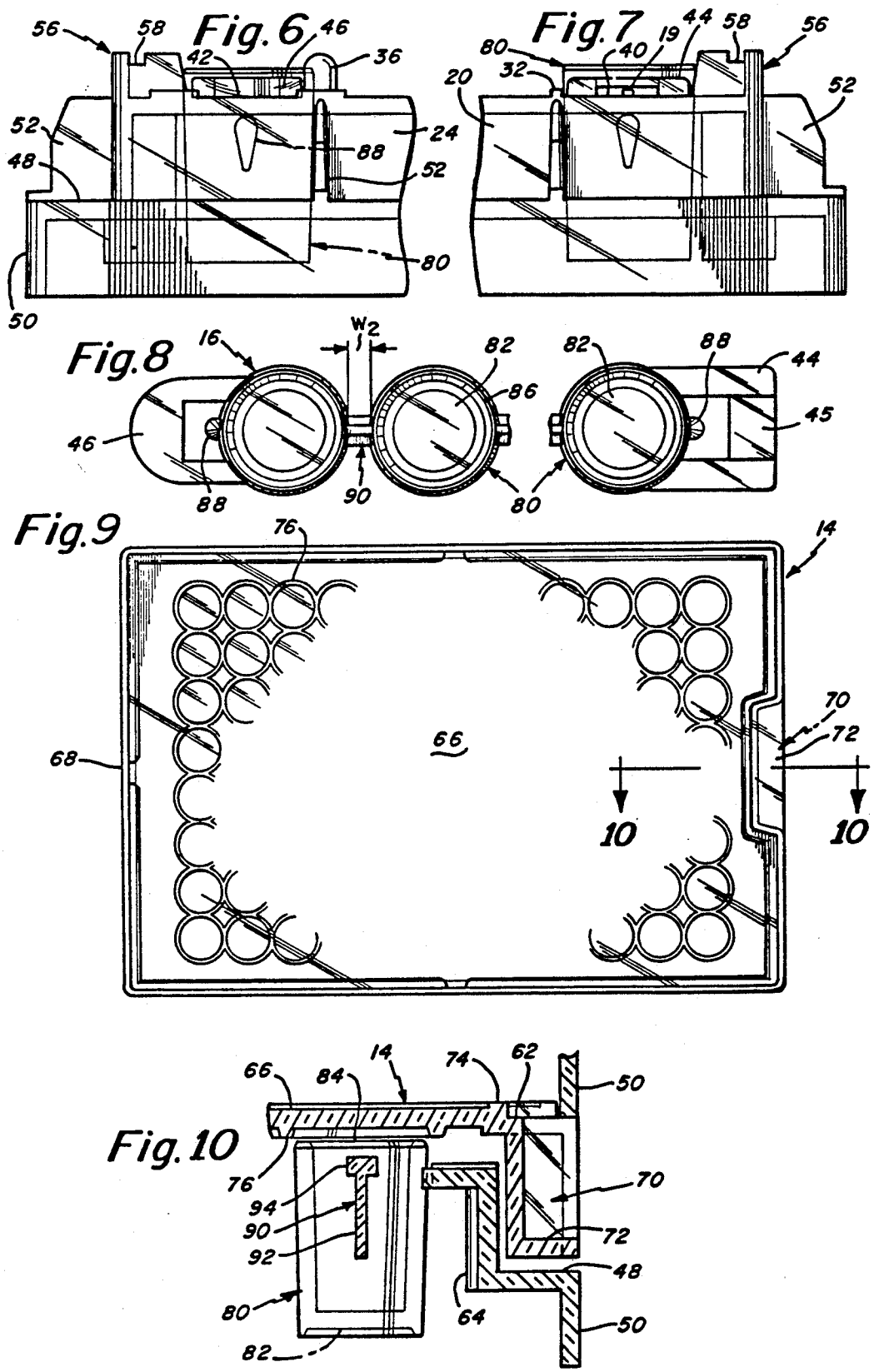

MULTI-WELL TEST PLATE

BACKGROUND OF THE INVENTION

This invention relates to a laboratory test plate having a plurality of chambers or wells and more particularly to such apparatus having a plurality of removable well strips wherein individual wells may be separated from the strips.

Multi-well test plates are used for holding a variety of test media in procedures such as cell growth, virus isolation, titration, toxicity tests, and other assays. Such plates typically include a base and cover and may further include means for separating one or more of the wells. See, for example, U.S. Pat. No. 4,154,795 to Thorne, U.S. Pat. No. 4,038,149 to Liner et.al., U.S. Pat. No. 3,907,505 to Beall et. al., and U.S. Pat. No. 3,649,464 to Freeman.

It has been suggested to provide a tray with a rectangular array of compartments for holding a multiplicity of individual microtest wells in U.S. Pat. No. 4,154,795 to Thorne. Each compartment is defined by four posts which engage the outer surfaces of a well disposed in the compartment. In one embodiment, all of the wells are molded integrally with one another by means of stems consisting of mold flashings so that the individual wells can be fitted into the compartments more rapidly. The stems are easily broken to enable one or more wells to be separated from each other when required. Alternatively, one or more rows of wells may be integrally connected to form a strip of wells.

The test plate described in Thorne is expensive to produce because the base tray requires an array of posts forming separate compartments for holding the wells in a fixed position. When removed from the base, the well strips tend to curve because the mold flashings cannot maintain the strip in a flat linear array. It is important that the wells be held flat, with the bottom surfaces of all wells in one plane, when taking an optical density reading through the bottom surfaces of the wells.

It has also been suggested to provide a rectangular frame having a central opening in which a plurality of separate well strips may be disposed. While the well strips may be removed from the base, the individual wells are rigidly connected such that they are not separable. The separation of individual wells is important where only some of the wells need to be subjected to further tests.

It is an object of this invention to provide a multi-well test plate which includes a plurality of removable well strips and a base.

Another object is to provide well strips which hold a plurality of wells in a fixed linear array whether or not the strips are disposed in the base.

A further object of this invention to provide such a plate wherein the wells are individually separable.

A still further object is to provide such a plate which is inexpensive to produce.

SUMMARY OF THE INVENTION

According to the invention, a multi-well test plate is provided which includes a base and a plurality of removable well strips. The base is a rectangular frame having four side walls which define a central aperture. One or more well strips are positionable within the central aperture of the frame and are held therein by mating means on the ends of each well strip and on the frame.

Each well strip consists of a linear array of wells which are joined by connecting means which maintain the wells in a flat linear relationship whether disposed in or separate from the base and which permit easy separation of individual wells. The connecting means is a T-shaped member disposed between two adjacent wells and which includes an elongated main rib longitudinally disposed between the wells and a shorter cross rib disposed transversely at one end of the main rib. The wells are easily severable by pulling apart the wells at their ends opposite the cross rib to cause the T-shaped member to break. This construction holds the wells rigidly in place and yet allows easy separation.

BRIEF DESCRIPTION OF THE DRAWINGS

FIG. 1 is an exploded perspective view of the test plate of this invention consisting of a base, well strips, and cover.

FIG. 2 is a top plan view of the base holding two well strips.

FIG. 3 is a bottom plan view of the base holding two well strips.

FIG. 4 is a sectional view taken along section lines 4—4 of FIG. 2 but with the cover on.

FIG. 5 is a sectional view taken along section lines 5—5 of FIG. 2.

FIG. 6 is a partial side elevation view taken along section lines 6—6 of FIG. 2.

FIG. 7 is a partial side elevation view taken along section lines 7—7 of FIG. 2.

FIG. 8 is a bottom plan view of the well strip.

FIG. 9 is a bottom plan view of the cover.

FIG. 10 is a sectional view taken along sections lines 10—10 of FIG. 9 but with stacking to show the cover recess for gripping.

DETAILED DESCRIPTION OF THE PREFERRED EMBODIMENT

A preferred embodiment of the test plate 10 of this invention, shown in FIG. 1, includes a base 12, cover 14, and one or more well strips 16. Preferably, each of the components is made of molded plastic and the well strips and cover are made of a transparent plastic to permit viewing of the contents of the well strips.

As shown in FIGS. 1-3, the base 12 consists of four vertical side walls 18, 20, 22, 24 which form a rectangular frame 26 having a central aperture 28. A horizontal top flange 30 extends inwardly from the top edges of the side walls on which is disposed a plurality of locating members 32, 36 for aligning and securing the well strips to the base. Also disposed on the top surface of the flange are raised alpha-numeric characters 17, 19 across two adjacent side edges 18, 20 to define the rows and columns, respectively, of a rectangular array within the central aperture.

The locating members 32, 36 on the base consist of ribs 32 disposed between the numerical column designations 19 above side wall 20, and pins 36 disposed in alignment with the ribs above opposing side wall 24. The ribs and pins define notches 40, 42 in which mating members 44, 46 on the opposing ends of the well strips fit. The mating members on the well strip consist of a rectangular flange 44 at one end which fits between the ribs on the frame and a rounded flange 46 on the opposing end which fits between the pins on the frame. In this manner, the well strip is positionable in the rectangular array defined by the frame in one direction only. Thus, if the well strip is removed from the frame, there is no ambiguity as to which end of the strip was in row A and which end in row H.

The well strip flange 46 has a recess 45 in its lower surface which accommodates the raised numeric character 19 (FIGS. 4, 8). Also, a ramped retaining member or snap 88 is provided on the side wall of the wells adjacent each of wellstrip flanges 44 and 46. These snaps 88 are pressure fit under base flange 30 to hold the strip in the base if the base is turned upside down (FIGS. 4, 8).

The base further includes a lower ledge 48 projecting horizontally from the lower end of the side walls and a peripheral lip 50 extending downwardly from the outer edge of the ledge. On each side of the four-sided ledge there is disposed a pair of vertical L-shaped members 52 for strengthening the base and aligning the cover on the base.

The base further includes notched posts 56 extending upwardly at each of the four corners of the side walls. The lower surface of the cover rests on the posts such that the posts hold the lip 68 of the cover slightly above the ledge 48 to permit insertion of a fingernail between the cover lip and ledge and thus allow ready removal of the cover from the base. Furthermore, by spacing the cover from the base air flow is permitted into and out of the base even with the cover in place. Also, by resting the cover on the posts, which are the highest vertical members on the base, the cover rests on the base at the same level whether or not there are strips disposed in the base.

The notches 58 on the posts 56 are for stacking one base upon another, as shown in phantom in FIG. 4. The bases are stacked one on top of the other without covers by nesting the ribs 60 extending downwardly from the lower surface of the side walls of the upper base into the notches 58 on the upper corners of the lower base. The ribs 60 are disposed within the lip 50 of the base and are shorter than the lip, i.e., they do not protrude below the lower edge of the lip.

Alternatively, as further shown in phantom in FIG. 4, a plurality of plates each consisting of a base and cover can be stacked one upon the other by nesting the lower edge of the lip 50 of the base on a peripheral groove 62 formed at the upper edge of the cover.

As shown in FIG. 5, spaced vertical ribs 64 are provided on the inner surface of the side walls for reinforcing the base.

The cover 14 consists of a horizontal top wall 66 having a downwardly extending peripheral lip 68. A notch 70 (see FIGS. 1 and 10) is cut out of one side wall of the lip and includes a horizontal bottom wall 72 to permit grasping and removal of an individual base and cover set from a stack of the same. The upper surface of the top wall has a raised peripheral ridge 74 defining a groove 62 for stacking a base on the cover as shown in FIG. 4. The lower surface of the top wall has an array of circular flanges 76 aligned with the open upper ends of the wells 80 to assist in viewing the contents of each well. Alternatively, each circular flange may contact the upper edge of a well to seal the same.

Each well strip 16 consists of a flat, linear array of eight wells 80 defining one column of the rectangular array of wells. By flat it is meant that the bottommost surfaces 86 of all wells in the strip lie in a horizontal plane. Each well strip has flanges 44, 46 at opposing ends for aligning and securing the strip in one direction only to the base.

Each cylindrical well 80 is open at the top and closed at the bottom by a bottom wall 82. The top edge 84 of each well is beveled. A peripheral ridge 86 extends downwardly from the bottom of each well to prevent scratches on the bottom well surface 82, which scratches would interfere with an optical reading of the well contents.

According to this invention, the individual wells are held in the strip by frangible T-shaped connecting members 90 between two adjacent wells. Each T-shaped member includes an elongated main rib 92 which extends vertically between the wells and, at the upper end of the main rib, a transverse and shorter cross rib 94 extending between the wells.

The T-shaped member extends from about 25% to about 75% of the height $H_1$ of the wells. It is disposed adjacent one end of the wells and preferably with the cross rib 94 spaced less than about 10% away from the open top ends 85 of the wells. Preferably, the height $H_2$ of the main rib 92 (measured parallel to the cylindrical axis of the wells) is up to about 50% of the height $H_1$ of the wells, while its thickness $T_2$ is less than about 25% of its height $H_2$, and the height $H_3$ of the cross rib 94 (measured parallel to the cylindrical axis of the wells) is up to about 25% of the height $H_2$ of the main rib, while its thickness $T_3$ is equal to or greater than its height $H_3$. In the specific embodiment shown: the wells are 0.475" in height $H_1$, 0.270" in outer diameter, and 0.040" in wall thickness; the main rib is 0.200" in height $H_2$ and 0.020" in thickness $T_2$; and the cross rib is 0.040" in height $H_3$ and 0.060" in thickness $T_3$. The width $W_2$ (measured from well-to-well) of the main rib varies from about 0.030" at its upper end to about 0.050" at its lower end (FIG. 8).

A well strip having these T-shaped connecting members is easily and inexpensively molded as an integral body of plastic. The T-shaped members hold the wells in a flat linear array with all bottom surfaces of the wells in a single plane. Thus, even when the well strip is removed from the base it constitutes a rigid member which is easily grasped and can be handled without curving or bending. Optical measurements are readily made on a row of wells because the bottom surfaces of all wells are held in one plane. In addition, by manually pulling apart adjacent wells at their ends disposed opposite the cross rib, the T-shaped member is easily broken permitting separation of individual wells.

In an alternative embodiment (not shown), the bottom of each well is provided with a microporous membrane rather than a solid bottom wall. The membrane may consist of a microporous plastic material. When a mixture of permeable and nonpermeable materials is placed in the wells, the permeable material is separated out by passing through the membrane. This separation is preferably accomplished by spinning individual wells in a centrifuge.

While a preferred embodiment of the invention has hereinbefore been described, it will be appreciated that variations of the invention will be perceived by those skilled in the art, which variations are nevertheless within the scope of the invention as defined by the claims appended hereto.

What is claimed is:

1. A multi-well test plate comprising:

a base comprising a four-sided rectangular frame having means defining a central opening between the four sides thereof, support means only on two opposite sides of the base for supporting a multi-well strip disposed in the opening and extending between the opposite sides while leaving individual wells of the strip unsupported, a multi-well strip comprising a plurality of spaced-apart wells arranged in a linear array and molded together as a strip of wells, each of said plurality of wells having side and bottom walls, wherein the bottom wall of each well is a microporous membrane, frangible connecting means joining pairs of adjacent wells and enabling each well to be readily separated from the other wells in the strip, the frangible connecting means also holding the wells with their bottom walls in a common plane when the strip is supported only at the ends thereof, and flanges attached to end wells of the strip and extending in opposite directions and releasably attachable to the support means for mounting the strip on the base.

2. The multi-well test plate of claim 1, wherein
the support means on the opposite sides of the base are dissimilar, and
the flanges on the end wells of the strips are dissimilar and each is capable of attaching to one of the dissimilar support means, respectively, on the base wherein the strip must be oriented in a prescribed direction when mounted on the base.

3. The multi-well test plate of claim 2, wherein
a plurality of support means are provided on each of the opposite sides of the base, all of the support means on one side being the same and dissimilar from the support means on the opposite side.

4. The multi-well test plate of claim 1, wherein
the frangible connecting means comprises a T-shaped member having and elongated main rib disposed vertically and a shorter cross rib disposed horizontally at one end of the main rib, the cross rib being disposed adjacent one of the top or bottom ends of the wells, and the wells being easily separable by pulling apart adjacent wells at the other of the top and bottom ends to break the T-shaped member.

* * * * *

UNITED STATES PATENT AND TRADEMARK OFFICE
CERTIFICATE OF CORRECTION

PATENT NO. : 5,084,246

DATED : January 28, 1992

INVENTOR(S) : George Lyman et al

It is certified that error appears in the above-indentified patent and that said Letters Patent is hereby corrected as shown below:

Column 2, line 37, after "gripping". insert --Fig. 11 is a fragmentary side plan view of a single well having a microporous membrane as the bottom wall--.

Column 4, line 51, delete "(not shown)" and insert --shown in Fig. 11--.

Column 6, line 18, delete "and" an insert --an--.

UNITED STATES PATENT AND TRADEMARK OFFICE
CERTIFICATE OF CORRECTION

PATENT NO. : 5,084,246
DATED : January 28, 1992
INVENTOR(S) : George Lyman et al It is certified that error appears in the above-indentified patent and that said Letters Patent is hereby corrected as shown below:

In the drawings, please add Fig. 11.

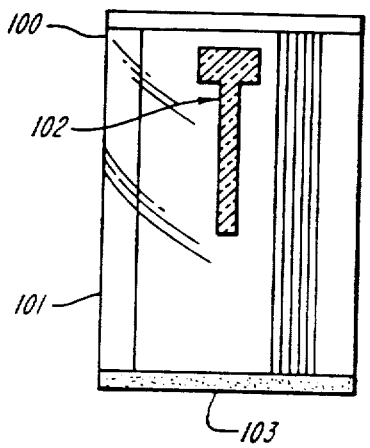

*FIG. 11*

Signed and Sealed this

Fourteenth Day of September, 1993

Attest:

BRUCE LEHMAN

*Attesting Officer*  *Commissioner of Patents and Trademarks*